BEGONIA PLANT
Filed Aug. 22, 1972 3 Sheets-Sheet 1
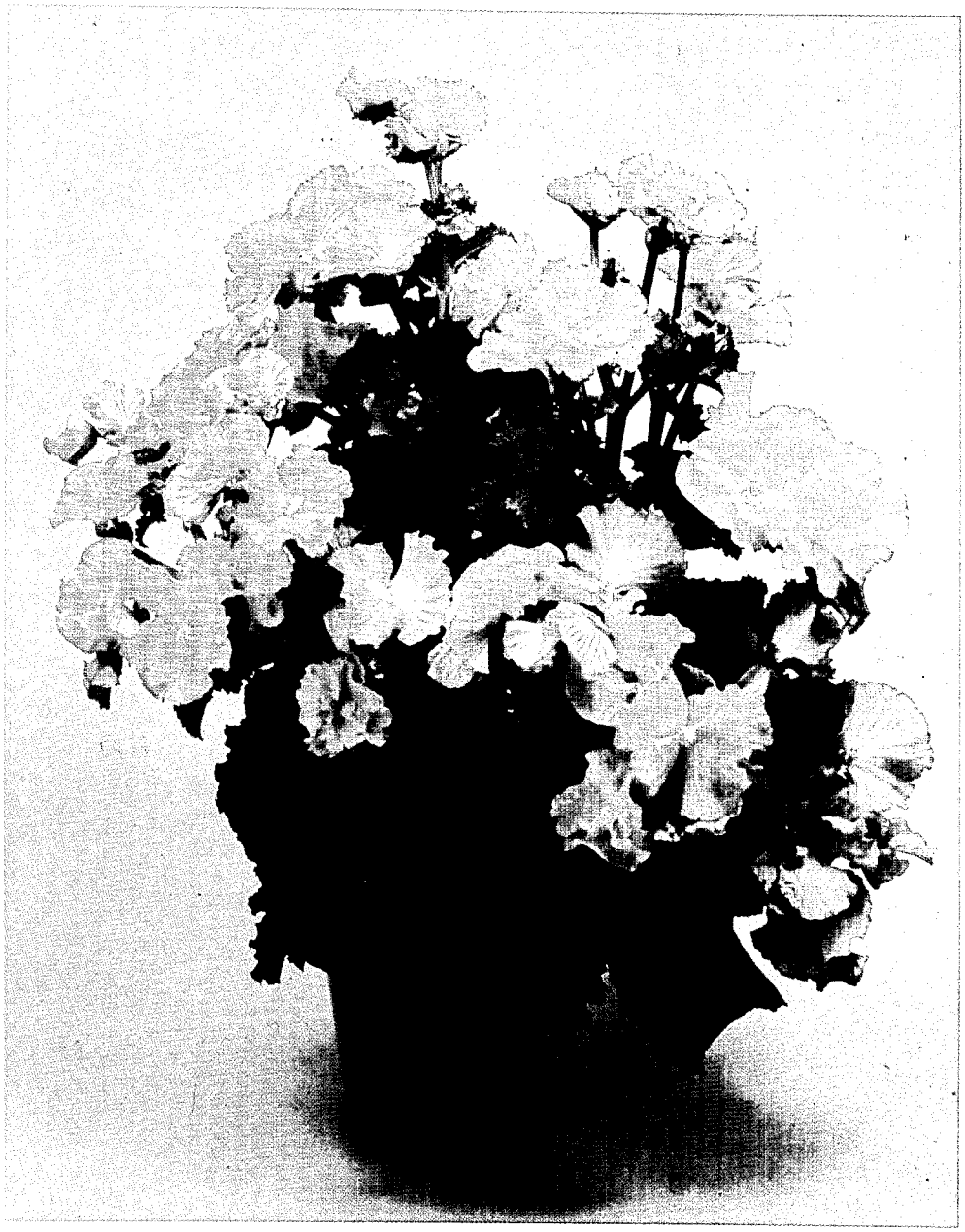

BEGONIA PLANT
Filed Aug. 22, 1972 3 Sheets-Sheet 2
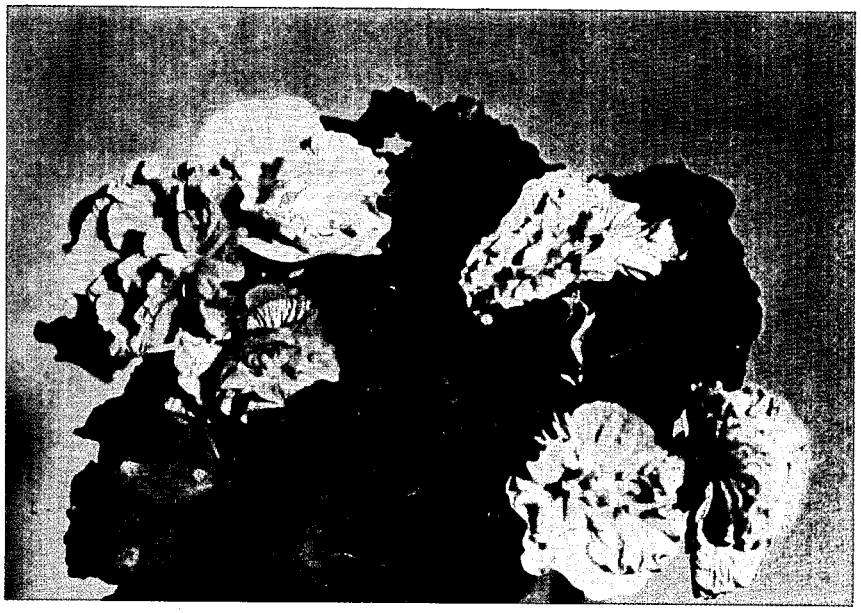

BEGONIA PLANT
Filed Aug. 22, 1972 3 Sheets-Sheet 3
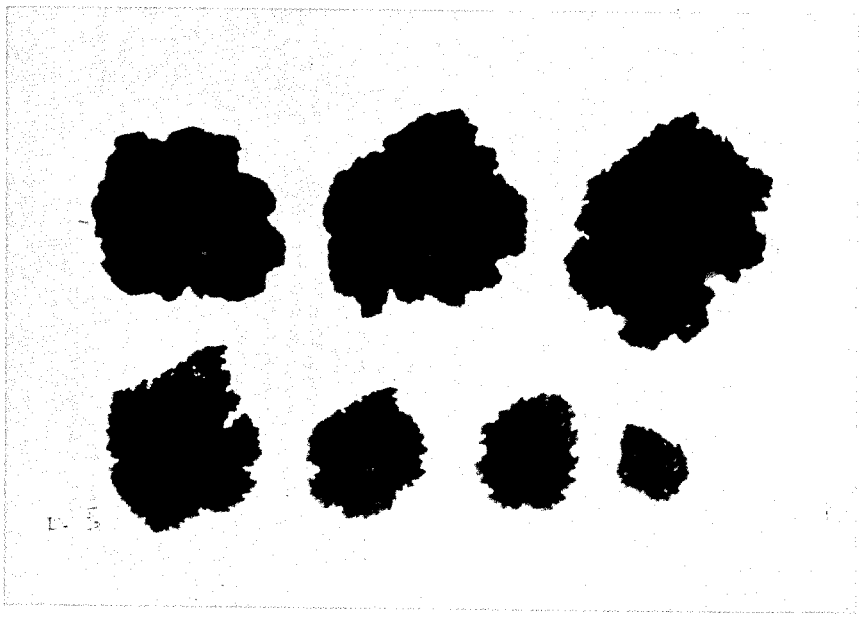

United States Patent Office

Plant Pat. 3,469
Patented Feb. 5, 1974

3,469
BEGONIA PLANT

Dieter Hayler, Endersbach, Germany, assignor to Mikkelsens, Inc., Ashtabula, Ohio Filed Aug. 22, 1972, Ser. No. 282,695
Int. Cl. A01h 5/00
U.S. Cl. Plt.—68 1 Claim The present invention relates to a new and distinctive variety of begonia plant botanically known as begonia elatior discovered by me as a mutation in flowing plants of the commercially known variety Riegers Schwabenland, disclosed and claimed in pending application for U.S. plant patent, Ser. No. 158,640, filed June 30, 1971, by Gertrude Rieger, legal representative of the deceased inventor Otto Rieger.

The new mutation was discovered in my nurseries at Endersbach, West Germany. By repeated asexual propagations of leaf cuttings it has been determined that this mutation retains its several unique characteristics. Additional propagations on a trial basis at the greenhouses of Mikkelsens, Inc., assignee of the present invention, in Ashtabula, Ohio, further substantiates that this discovery asexually propagates true to type in other areas having different climatic conditions.

The most distinguishing characteristics of this new variety when compared with the parent variety is the ruffled camellia type flowers, the leaves with ruffled or wavy edges, the extra heavy crisp texture of the foliage, thick heavy stems, and a salmon red color in the flower bracts.

The following features distinguish the new variety of this type from both its parent and other commercial begonia varieties of this type known and used in the commercial floriculture industry:

(1) Plants are extremely vigorous, can be readily overgrown giving a clumsy appearance. Keeping the soil nutrients at a low level corrects this type of growth.

(2) Foliage is heavy, and often has a very crisp texture.

(3) Internodal spacing is quite short allowing for development of a very compact plant.

(4) Foliage is comparable in size to Schwabenland. However, the wavy edges of the leaves tend to be associated with a cupping characteristic of the leaf as if a draw string were being pulled to form a closure.

(5) The immature foliage is dark green with some red pigmentation throughout the upper surface and with greater amounts on the reverse side. Leaf petioles are thicker than those of the parent variety under similar environmental conditions.

(6) The new variety produces somewhat less flowers than Schwabenland, but the large size of the flowers compensates for any shortage in flower quantity.

(7) The camellia type flower in this mutation is very distinctive in comparison to any of the Rieger Schwabenland types. Tuberous type begonias are known to have camellia and carnation type flowers but there are not any in commercial production known to have the same form as in this new mutation. The bracts are much thicker and stiffer, with a corrugated texture in comparison to most commercial varieties.

(8) The flower color is distinctively different than the parent or any other known mutations in the Schwabenland series.

(9) Asexual reproduction is readily accomplished by propagating leaf cuttings. The development of adventitious shoots is considerably slower than for other commercial cultivars of this type. A slower rate of overall growth necessitates somewhat larger quantities of stock plants needed for leaf production for propagating purposes.

(10) Leaf chlorosis is somewhat prevalent if proper levels of minor elements are not maintained in synthetic growing media as compared to other similar mutations from Schwabenland.

The new variety is illustrated in the accompanying colored photographic drawings in which Sheet 1 is a typical commercially grown plant comprising the present invention; Sheet 2 is a closeup of a flower cluster, and Sheet 3 illustrates a typical foliage pattern in various stages of development from young to mature leaves. Colors of foliage and flowers are as true as is reasonably possible to produce in color photography of this type.

The following detailed description of the new variety is based on several seasonal observations and critical analysis of a large number of plants propagated from leaf cuttings and grown under typical commercial glasshouse practices in Endersbach, West Germany. As is the case with nearly all plant materials, natural light, temperatures, and other environmental factors may alter the rate of growth; the form and size of the foliage; the size, texture, shape, quantity, quality, and color intensity of the flowers. The description which follows is based on normal production techniques commonly used for begonias of this type in Germany unless otherwise noted. Color references are to the Royal Horticultural Society Color Chart, except where general color terms of ordinary dictionary significance are applied.

Parentage: A mutation of Riegers Schwabenland.

Propagation: By asexually propagating several thousand leaf cuttings, selecting those leaves that rooted and developed basal adventitious bud shoots, and subsequently flowering those plants, it has been repeatedly demonstrated that the mutation is stable and produces true to type under varying climatic environments.

Rooting habits: Rapid and voluminous development of roots is similar to Rieger Schwabenland with the development of basal adventitious bud shoots being slower than in the original variety.

Plant form: Plants tend to be very compact.

Habit of growth: The mutation is extremely vigorous, with heavy generally upright stems, and close internodes. Some self branching and heavy leaf petioles add to the very compact appearance. This is to date the most vigorous mutation originating from any of the Rieger Schwabenland varieties. Plants grown in dull cool environments occasionally develop stem and leaf fasciation.

Blooming habit: Flowers have semi-double appearance with generally four bracts. Blooms flower one at a time carried on trusses. The total blooming period carries over for two to four months. Individual blooms will flourish for sevral weeks giving the plant an ongoing array of color. The number of blooms will vary with the seasons of the year, the age of the plant, and other related factors.

Blooming season: In Germany the natural flowering season of this mutation is slightly later than for the parental cultivar Schwabenland which normally flowers late November or early December. When proper regulation of the photo period is applied in conjunction with proper temperature manipulations of the young plants, the new begonia variety can be brought into flower at any season of the year, which characteristic is of great economic importance to the commercial flower producer. The soft salmon red color of the bracts is acceptable in all seasons of the year. The semi-cupped, wavy edged leaves compliment the ruffled edge camellia type bracts of the blooms.

Foliage: The foliage of the mutation is quite distinct with a frilled wavy edge. The semi-cupped appearance of individual leaves is a definite characteristic. The foliage is borne alternately at a tight angle to the stem; is above average in quantity; tending to be thick, and somewhat rigid with heavy, stiff petioles.

*Size.*—Foliage would be classified as being average in size for this type of begonia. Environmental conditions can greatly alter the size, shape, texture of the foliage.

*Shape.*—The shape of the foliage of this begonia tends to be somewhat oval and less heart shaped and pointed. The frilled wavy edges reduce any sharp indentations. The colored photograph clearly portrays the general oval shape. The overall leaf surface is undulated and not flat.

*Texture.*—The upper surface is quite waxy, smooth, and resilient. The edges have a raspy feel to the touch. The under surface is smooth and glossy with a highly reflective appearance.

*Margins.*—The wavy or undulating characteristic of the foliage tends to eliminate any distinctive indentations of the leaf margins. The edges are finely rippled as on a coarse file. The margins resemble being pulled together as with a draw string.

*Color.*—Foliage as illustrated has a red edge and is quite crumpled looking. Generally the foliage will be an overall dark green. New foliage: Upper side: yellow-green RHS 146–A. Underside: toward yellow-green RHS 146–C with intermixing of red pigmentation. Old foliage: Upper side: is between yellow-green RHS 147–A and green RHS 137–A. Underside: is nearly yellow-green RHS 148–A.

*Plant stems.*—Are quite thick, more so than the average stems of commercial begonias of this type. Very vigorous. Color is light green with diffused red pigmentation where exposed to some light

*Disease resistance.*—The foliage is quite resistant to common powdery mildew infections when compared to melior type begonias. The foliage does show minor element deficiencies more rapidly than the original Schwabenland variety Flowers: Flowers are borne singly on a trussing stem. The individual flower pedicels are quite thick and heavy giving unusual support to the flower. Bracts are corrugated, heavy textured, and tend to be cupped rather than laying flat as in Schwabenland, yet have a graceful appearance. Individual blooms are generally larger than those of the parent variety and often measure above 8 centimeters in diameter. Flowers are almost completely male, with a distinctive yellow eye made up of a cluster of stamens and anthers. Bracts are quite rugged to handling

*Quantity.*—Quite floriferous but less so that the original variety, usually taking a considerably longer time to develop mature flowers. Flowering development will continue for several months. Lower quantity of flowers is offset by larger individual flowers and the distinctive flower form

*Buds.*—Are flatly folded and progressively develop as the peduncle continues to elongate and initiates new flowering parts. The flower bud is typically the shape of a lima bean but ultimately develops into a quite symmetrical flower

*Petals (bracts).*—Upper side: from dark Red RHS 43–A to lighter Red RHS 44–C; underside: near Red RHS 40–A

*Reproductive organs.*—Flowers are very predominately male; to date no female flowers have been observed. Stamens: are near orange-yellow RHS 25–B and give a good contrast to the salmon red bracts. Pollen: is a light yellow RHS 13–C or RHS 14–C No styles or ovaries have been observed.

I claim:

1. A novel and distinctive elatior begonia cultivar which is a mutation of the cultivar Schwabenland, the new cultivar being characterized particularly by its salmon red colored, ruffled camellia type flowers having unusually heavy textured bracts and carried on strong, thick pedicels originating from an unusually heavy peduncle; foliage which has an overall wavy or undulating surface, and raspy edges, with the foliage being considerably thicker than average begonia foliage, and quite resistant to powdery mildew; by its tight compact growth associated with close internodes, heavy thick stems, and heavy thick leaf petioles; by its vigorous growth habit, and by its ability to be produced year around under controlled environmental conditions.

No references cited.

ROBERT E. BAGWILL, Primary Examiner

UNITED STATES PATENT OFFICE
CERTIFICATE OF CORRECTION

Patent No. PP-3469 Dated February 5, 1974

Inventor(s) DIETER HAYLER

It is certified that error appears in the above-identified patent and that said Letters Patent are hereby corrected as shown below:

Column 1, line 11, change "flowing" to --flowering--.

Column 2, line 51, change "sevral" to --several--.

Signed and sealed this 23rd day of July 1974.

(SEAL)
Attest:

McCOY M. GIBSON, JR.
Attesting Officer

C. MARSHALL DANN
Commissioner of Patents

USCOMM-DC 60376-P69
* U.S. GOVERNMENT PRINTING OFFICE 1969 O—366-334